(12) United States Patent
Hou et al.

(10) Patent No.: US 9,738,613 B2
(45) Date of Patent: Aug. 22, 2017

(54) SUBSTITUTED 1,2,3-TRIAZOLES AS ANTITUMOR AGENTS

(71) Applicant: National Central University, Taoyuan (TW)

(72) Inventors: Duen-Ren Hou, Taipei (TW); Sharada Prasanna Swain, Bhirang (IN)

(73) Assignee: National Central University, Jhongli (TW)

( * ) Notice: Subject to any disclaimer, the term of this patent is extended or adjusted under 35 U.S.C. 154(b) by 0 days.

(21) Appl. No.: 14/715,019

(22) Filed: May 18, 2015

(65) Prior Publication Data

US 2016/0340321 A1    Nov. 24, 2016

(51) Int. Cl.
  *C07D 249/04* (2006.01)
  *A61K 31/4192* (2006.01)
  *A61P 35/04* (2006.01)

(52) U.S. Cl.
  CPC ................... *C07D 249/04* (2013.01)

(58) Field of Classification Search
  CPC .................. A61K 31/4192; C07D 249/04
  See application file for complete search history.

(56) References Cited

U.S. PATENT DOCUMENTS 8,461,209 B2 * 6/2013 Yoshida ............... C07C 311/51
  514/601

FOREIGN PATENT DOCUMENTS

CN    103339115 A    10/2013

OTHER PUBLICATIONS

Stella (J. Pharmaceutical Sciences, 2010, 99(12), pp. 4755-4765).*
Office Action of corresponding TW application, published on Mar. 1, 2017.

* cited by examiner

*Primary Examiner* — Susanna Moore
(74) *Attorney, Agent, or Firm* — Wang Law Firm, Inc.

(57) ABSTRACT

Compounds represented by Formula I:

Formula I

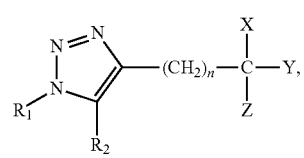

and/or a pharmaceutically acceptable salts, a prodrug, a solvate and a combination thereof, a pharmaceutical composition including the triazole derivative, and a method of treating a cancer disease in an individual are disclosed.

1 Claim, No Drawings

SUBSTITUTED 1,2,3-TRIAZOLES AS ANTITUMOR AGENTS

BACKGROUND OF THE INVENTION

Field of the Invention

The invention relates to a field of novel compounds which have antineoplastic activity. More specifically, the invention relates to substituted 1,2,3-triazoles which have antineoplastic activity, a pharmaceutical composition including the same, and a method of treating a cancer disease in an individual.

Description of Related Art

Cancer, also known as a malignant tumor or malignant neoplasm, is a group of diseases involving abnormal cell growth with the potential to invade or spread to other parts of the body, and remains one of the most important unmet medical challenges to mankind Cancer can be treated by surgery, chemotherapy, radiation therapy, hormonal therapy, and targeted therapy (including immunotherapy such as monoclonal antibody therapy), or any combination of these approaches. The choice of therapy depends upon the location and grade of the tumor and the stage of the disease, as well as the general state of the patient(performance status).

Among these approaches, chemotherapy is widely used for all types of cancers, in particular for those inoperable or with metastatic characteristics. Although a variety of chemotherapeutic compounds are used in clinics, tumors and their metastasis become refractory to chemotherapy when the tumor cells develop the ability of multidrug resistance. In some cases, the tumors are inherently resistant to some classes of chemotherapeutic agents. In other cases, the acquired resistance against chemotherapeutic agents is developed during the chemotherapeutic intervention.

Therefore, there remain significant limitations to the efficacy of available chemotherapeutic compounds in treating different classes of tumors, and thus there remains a need for new chemotherapeutic agents.

A triazole (Htrz) refers to either one of a pair of isomeric chemical compounds with molecular formula $C_2H_3N_3$, having a five-membered ring of two carbon atoms and three nitrogen atoms. The five membered triazole ring exists in two tautomeric forms i.e. 1,2,3-triazole and 1,2,4-triazole. Both 1,2,3-triazole and 1,2,4-triazole and their derivatives are of great importance in medicinal chemistry and can be used for the synthesis of numerous heterocyclic compounds with different biological activities such as antiviral, antibacterial, antifungal, antituberculosis, anticonvulsant, antidepressant, anti-inflammatory, anticancer activities, etc. They have been reported to be inhibitors of glycogen synthase kinase-3, antagonists of GABA receptors, agonists of muscarine receptors, neuroleptic agent, and these compounds also show anti-HIV-1, cytotoxic, antihistaminic, and antiproliferative activities.

Thus, the design and synthesis of novel triazole derivatives are the prospective direction of medicinal chemistry for the scientists working in this field.

Based on common technical knowledge in the art, the compound may change greatly in stereostructure, spatial effect and electronic effect when the types and number of the substitutes and the substituted atomic species are different, thereby generating a great impact on the physicochemical property and pharmaceutical active thereof Thus, herein we describe the synthesis and anticancer activity of new substituted 1,2,3-triazoles which types and number of the substitutes thereof are different form existing substituted 1,2,3-triazoles.

SUMMARY OF THE INVENTION

It is an object of the invention to provide compounds that are useful in treating cancer or disease characterized by undesirable cell proliferation. To achieve the object, the present invention provides a compound represented by Formula I:

Formula I

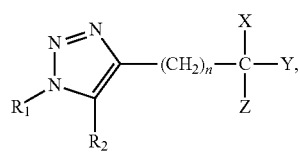

wherein in Formula I, $R_1$ may be independently selected from H, a substituted or unsubstituted $C_{1-20}$ alkyl, a substituted or unsubstituted $C_{4-9}$ cycloalkyl, a substituted or unsubstituted $C_5$-$C_9$ aryl, a substituted or unsubstituted $C_{4-9}$ heteroaryl; $R_2$ may be independently selected from H, a substituted or unsubstituted $C_{1-20}$ alkyl, a substituted or unsubstituted $C_{4-9}$ cycloalkyl, and a substituted or unsubstituted $C_5$-$C_9$ aryl; X, Y and Z are each independently selected from H, a hydroxy, a thiohydroxy, a carbonyl, a sulfonyl, a sulfamoyl, a carbamoyl, a ureido, an amido, a $C_{1-4}$ alkyl alcohol, a $C_{1-4}$ alkylsulfonyl, a $C_{1-4}$ alkylamino, a $C_{2-4}$ alkoxy, a $C_{1-4}$ alkoxycarbonyl, a $C_{1-4}$ alkoxylcarbamoyl, a $C_{1-4}$ haloalkyl, a $C_{1-4}$ haloalkylthio, and a $C_{1-4}$ haloalkylsulfonyl; wherein at least one substituent of the substituted $C_{1-20}$ alkyl, the substituted $C_{4-9}$ cycloalkyl, the substituted $C_5$-$C_9$ aryl or the substituted $C_{4-9}$ heteroaryl is selected from a halogen atom, a hydroxy, a cyano, a nitro, a thiohydroxy, an amino, a carbonyl, a carbamoyl, a sulfamoyl, a $C_{1-20}$ alkyl, a $C_{2-20}$ alkenyl, a $C_{2-20}$ alkynyl, a $C_{1-20}$ alkoxy, a $C_{1-20}$ alkyl alcohol, a $C_{1-20}$ haloalkyl, a $C_{1-20}$ haloalkylthio, a $C_{1-20}$ alkylamino, a $C_{1-20}$ alkylamido, a $C_{1-20}$ alkylsulfonyl, a $C_{1-20}$ haloalkylsulfonyl, a $C_{1-20}$ alkoxycarbonyl or a $C_{1-20}$ alkoxylcarbamoyl, a $C_{5-9}$ aryl, a $C_{4-9}$ cycloalkyl, a $C_{4-9}$ heteroaryl, and a $C_{3-10}$ heterocycloalkyl, and n is 0, 1, 2, 3, 4 or 5; and/or a pharmaceutically acceptable salts, a prodrug, a solvate and a combination thereof.

In a preferred embodiment of the compounds described above, $R_2$ may be H and $R_1$ may be independently selected from H, a substituted or unsubstituted $C_{1-20}$ alkyl, a substituted or unsubstituted $C_{4-9}$ cycloalkyl, a substituted or unsubstituted thienyl, a substituted or unsubstituted pyridyl and a substituted or unsubstituted phenyl.

In a preferred embodiment of the compounds described above, $R_1$ may be a substituted or unsubstituted $C_{1-20}$ alkyl and $R_2$ may be H.

In a preferred embodiment of the compounds described above, X, Y and Z may be each independently selected from a hydroxy, an amino, a $C_{1-4}$ alkylamino, and a $C_{2-4}$ alkoxy.

In a preferred embodiment of the compounds described above, the compound may be one of compound shown below:

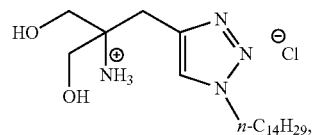

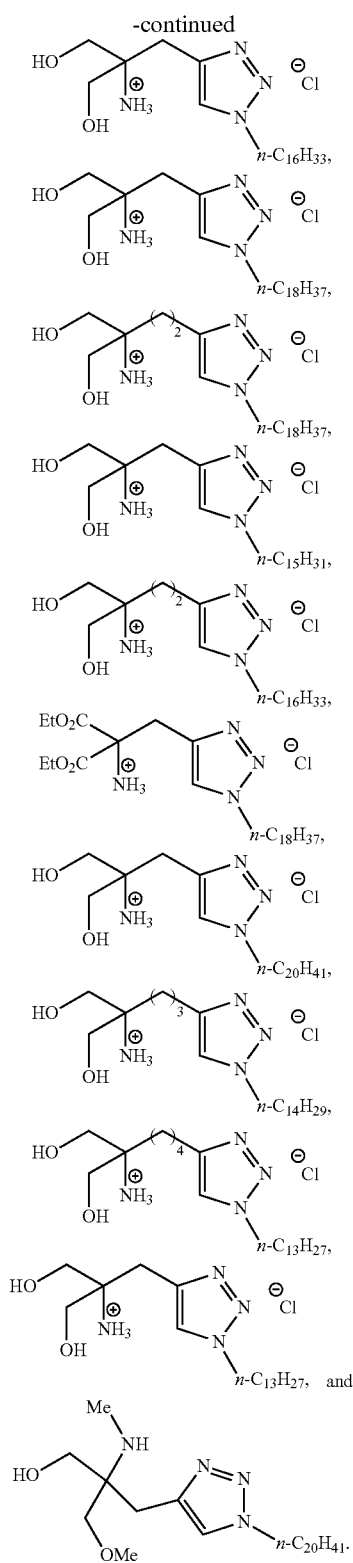

It is another object of the invention to provide a pharmaceutical composition which may include at least one of the triazole derivatives described above and a carrier.

In a preferred embodiment of the pharmaceutical composition described above, the pharmaceutical composition may further comprise an additive, and the additive may be a filler, a wetting agent, a binder, or a disintegrant.

In a preferred embodiment of the pharmaceutical composition described above, the pharmaceutical composition may be in the form of tablets, capsules, powders, granules, suppositories, reconstitutable powders, liquid preparations for oral administration, nasal aerosols or inhalation compositions, or sterile injectable compositions.

It is another object of the invention to provide a method of treating a cancer disease in an individual, comprising administering to the mammal a therapeutically effective amount of the pharmaceutical composition described above.

In a preferred embodiment of the method described above, the cancer disease may be a prostate cancer, and the prostate cancer may have metastasized to a tissue selected from the group consisting of bone, lymph node, eye, pancreas, lung, adrenal gland, breast, kidney, muscle, salivary gland, spleen, brain and/or liver.

In a preferred embodiment of the method described above, the pharmaceutical composition may be administered by oral, intravenous, intramuscular, subcutaneous, or rectal administration.

With these and other objects, advantages, and/or features of the invention that may become hereinafter apparent, the nature of the invention may be more clearly understood by reference to the detailed description of the invention.

DETAILED DESCRIPTION OF THE PREFERRED EMBODIMENTS

Exemplary embodiments of the present invention are described herein in the context of a compound represented by Formula I, a pharmaceutical composition comprising the compound of Formula I, and a method of treating a cancer disease in an individual.

As used herein, the term "and/or" includes any and all combinations of one or more of the associated listed items. Expressions such as "at least one of," when preceding a list of elements, modify the entire list of elements and do not modify the individual elements of the list.

The term "therapeutically effective amount" as used herein and in the claims is intended to mean that amount of active compound or pharmaceutical agent that elicits the biological or medicinal response in a tissue, system, animal or human that is being sought by a researcher, veterinarian, medical doctor or other clinician.

The term "pharmaceutically acceptable salt" as used herein and in the claims is intended to include nontoxic base addition salts. Suitable salts include those derived from organic and/or inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxy-substituted alkylamines such as diethanolamine, triethanolamine or tris(hydroxymethyl)-aminomethane), or with bases such as piperidine or morpholine.

The term "prodrug" as used herein and in the claims is intended to mean any form of a drug (or compound) which is administered to an organism, such as a human, in an inactive or less active form and is converted, e.g. by metabolization, into the active form. Said conversion of the prodrug into the active form is not specifically restricted and includes any chemical and/or physical alteration of the prodrug which occurs after administration, such as for example release of an active part (particularly the cytostatic agent) of the prodrug at the site of action. The prodrug used herein is not especially restricted as long as a compound represented by Formula I is satisfied:

Formula I

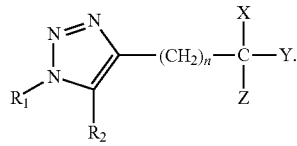

In Formula I, $R_1$ may be independently selected from H, a substituted or unsubstituted $C_{1-20}$ alkyl, a substituted or unsubstituted $C_{4-9}$ cycloalkyl, a substituted or unsubstituted $C_5$-$C_9$ aryl, and a substituted or unsubstituted $C_{4-9}$ heteroaryl. $R_2$ may be independently selected from H, a substituted or unsubstituted $C_{1-20}$ alkyl, a substituted or unsubstituted $C_{4-9}$ cycloalkyl, and a substituted or unsubstituted $C_5$-$C_9$ aryl. X, Y and Z may be each independently selected from H, a hydroxy, a thiohydroxy, a carbonyl, a sulfonyl, a sulfamoyl, a carbamoyl, a ureido, an amino, an amido, a $C_{1-4}$ alkyl alcohol, a $C_{1-4}$ alkylsulfonyl, a $C_{1-4}$ alkylamino, a $C_{2-4}$ alkoxy, a $C_{1-4}$ alkoxycarbonyl, a $C_{1-4}$ alkoxylcarbamoyl, a $C_{1-4}$ haloalkyl, a $C_{1-4}$ haloalkylthio, and a $C_{1-4}$ haloalkylsulfonyl. At least one substituent of the substituted $C_{1-20}$ alkyl, the substituted $C_{4-9}$ cycloalkyl, the substituted $C_5$-$C_9$ aryl and the substituted $C_{4-9}$ heteroaryl may be selected from a halogen atom, a hydroxy, a cyano, a nitro, a thiohydroxy, an amino, a carbonyl, a carbamoyl, a sulfamoyl, a $C_{1-20}$ alkyl, a $C_{2-20}$ alkenyl, a $C_{2-20}$ alkynyl, a $C_{1-20}$ alkoxy, a $C_{1-20}$ alkyl alcohol, a $C_{1-20}$ haloalkyl, a $C_{1-20}$ haloalkylthio, a $C_{1-20}$ alkylamino, a $C_{1-20}$ alkylamido, a $C_{1-20}$ alkylsulfonyl, a $C_{1-20}$ haloalkylsulfonyl, a $C_{1-20}$ alkoxycarbonyl or a $C_{1-20}$ alkoxylcarbamoyl, a $C_{5-9}$ aryl, a $C_{4-9}$ cycloalkyl, a $C_{4-9}$ heteroaryl, and a $C_{3-10}$ heterocycloalkyl, and n may be 0, 1, 2, 3, 4 or 5.

The term "solvate" as used herein and in the claims is intended to mean to a complex of variable stoichiometry formed by a solute and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water.

According to an aspect of the present embodiments, there is provided a compound represented by Formula 1 below:

Formula I

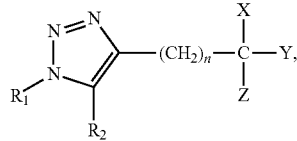

wherein in Formula I, $R_1$ may be independently selected from H, a substituted or unsubstituted $C_{1-20}$ alkyl, a substituted or unsubstituted $C_{4-9}$ cycloalkyl, a substituted or unsubstituted $C_5$-$C_9$ aryl, and a substituted or unsubstituted $C_{4-9}$ heteroaryl; $R_2$ may be independently selected from H, a substituted or unsubstituted $C_{1-20}$ alkyl, a substituted or unsubstituted $C_{4-9}$ cycloalkyl, and a substituted or unsubstituted $C_5$-$C_9$ aryl; X, Y and Z may be each independently selected from H, a hydroxy, a thiohydroxy, a carbonyl, a sulfonyl, a sulfamoyl, a carbamoyl, a ureido, an amido, a $C_{1-4}$ alkyl alcohol, a $C_{1-4}$ alkylsulfonyl, a $C_{1-4}$ alkylamino, a $C_{2-4}$ alkoxy, a $C_{1-4}$ alkoxycarbonyl, a $C_{1-4}$ alkoxylcarbamoyl, a $C_{1-4}$ haloalkyl, a $C_{1-4}$ haloalkylthio, and a $C_{1-4}$ haloalkylsulfonyl; wherein at least one substituent of the substituted $C_{1-20}$ alkyl, the substituted $C_{4-9}$ cycloalkyl, the substituted $C_5$-$C_9$ aryl or the substituted $C_{4-9}$ heteroaryl may be selected from a halogen atom, a hydroxy, a cyano, a nitro, a thiohydroxy, an amino, a carbonyl, a carbamoyl, a sulfamoyl, a $C_{1-20}$ alkyl, a $C_{2-20}$ alkenyl, a $C_{2-20}$ alkynyl, a $C_{1-20}$ alkoxy, a $C_{1-20}$ alkyl alcohol, a $C_{1-20}$ haloalkyl, a $C_{1-20}$ haloalkylthio, a $C_{1-20}$ alkylamino, a $C_{1-20}$ alkylamido, a $C_{1-20}$ alkylsulfonyl, a $C_{1-20}$ haloalkylsulfonyl, a $C_{1-20}$ alkoxycarbonyl or a $C_{1-20}$ alkoxylcarbamoyl, a $C_{5-9}$ aryl, a $C_{4-9}$ cycloalkyl, a $C_{4-9}$ heteroaryl, and a $C_{3-10}$ heterocycloalkyl, and n may be 0, 1, 2, 3, 4 or 5; or a pharmaceutically acceptable salts, prodrugs, solvates and a combination thereof.

A substituent in the compound of Formula 1 will now be described in detail.

In an embodiment, $R_1$ and $R_2$ in Formula 1 may be identical to each other.

In another embodiment, $R_2$ in Formula 1 may be H and $R_1$ in Formula 1 may be independently selected from H, a substituted or unsubstituted $C_{1-20}$ alkyl, a substituted or unsubstituted $C_{4-9}$ cycloalkyl, a substituted or unsubstituted thienyl, a substituted or unsubstituted pyridyl and a substituted or unsubstituted phenyl.

In some other embodiments, $R_1$ may be selected from a substituted or unsubstituted $C_{1-20}$ alkyl and $R_2$ may be H.

In an embodiment, X, Y and Z may be each independently selected from a hydroxy, an amino, a $C_{1-4}$ alkylamino, and a $C_{2-4}$ alkoxy.

Hereinafter, the definition of representative substituents used herein will now be described in detail (In this regard, numbers of carbons limiting a substituent are non-limited, and thus the substituent characteristics are not limited).

The term "Me" as used herein refers to a methyl, and the term "Et" as used herein refers to an ethyl.

The term "$C_{1-20}$ alkyl" as used herein and in the claims (unless specified otherwise) means a saturated aliphatic hydrocarbon including straight chain and branched chain groups, and such a hydrocarbon with 1 to 20 carbon atoms (whenever a numerical range; e.g., "1-20", is stated herein, it means that the group, in this case the alkyl may contain 1 carbon atom, 2 carbon atoms, 3 carbon atoms, etc. up to and including 20 carbon atoms). Non-limiting examples of the unsubstituted $C_1$-$C_{20}$alkyl are a methyl, an ethyl, a propyl, an iso-butyl, a sec-butyl, a pentyl, an iso-amyl, a hexyl, a heptyl, an octyl, a nonanyl, and a dodecyl. At least one hydrogen atom of the unsubstituted $C_1$-$C_{20}$ alkyl may be substituted with a deuterium atom, a halogen atom, a hydroxyl, a nitro, a cyano, an amino, an amidino, a hydrazine, a hydrazone, a carboxyl or a salt thereof, a sulfonic acid group or a salt thereof, a phosphoric acid group or a salt thereof, a $C_1$-$C_{10}$ alkyl, a $C_1$-$C_{10}$ alkoxy, a $C_2$-$C_{10}$ alkenyl, a $C_2$-$C_{10}$ alkynyl, a $C_6$-$C_{16}$ aryl, or a $C_1$-$C_{16}$ heteroaryl.

The term "$C_{2-20}$ alkenyl" as used herein and in the claims (unless specified otherwise) means an alkyl, as defined herein, having at least one carbon-carbon double bond in the center or at a terminal thereof. Examples of the unsubstituted $C_2$-$C_{20}$ alkenyl are an ethenyl, a propenyl, a butenyl, and the like. At least one hydrogen atom of the unsubstituted alkenyl may be substituted with the same substituent as used in the substituted alkyl described above.

The term "$C_{2-20}$ alkynyl" as used herein and in the claims (unless specified otherwise) means an alkyl, as defined herein, having at least one carbon-carbon triple bond in the center or at a terminal of thereof. Examples of the unsubstituted $C_2$-$C_{20}$ alkynyl are acetylenyl, propynyl, phenylacetylenyl, naphthylacetylenyl, isopropylacetylenyl, t-butylacetylenyl, diphenylacetylenyl, and the like. At least one hydrogen atom of the unsubstituted $C_2$-$C_{20}$ alkynyl may be substituted with the same substituent as used in the substituted alkyl.

The term "$C_{5-9}$ aryl" as used herein and in the claims (unless specified otherwise) means an all-carbon monocyclic or fused-ring polycyclic (i.e., rings which share adjacent pairs of carbon atoms) having 5 to 9 carbon atoms and a completely conjugated pi-electron system.

The term "$C_{4-9}$ cycloalkyl" as used herein and in the claims (unless specified otherwise) means an all-carbon monocyclic or fused ring (i.e., rings which share and adjacent pair of carbon atoms) with 4 to 9 carbon atoms, wherein one or more rings do not have a completely conjugated pi-electron system. Examples, without limitation, of cycloalkyl are cyclopropyl, cyclobutyl, cyclopentyl, cyclopentyl, cyclohexyl, cyclohexadienyl, cycloheptyl, and cycloheptatrienyl.

The term "$C_{4-9}$ heteroaryl" as used herein and in the claims (unless specified otherwise) means a monocyclic or fused ring (i.e., rings which share an adjacent pair of atoms) having 4 to 9 carbon atoms and in the ring(s) one or more atoms selected from the group consisting of N, O and S and, in addition, having a completely conjugated pi-electron system.

The term "$C_{3-10}$ heterocycloalkyl" as used herein and in the claims (unless specified otherwise) means a monocyclic or fused ring (i.e., rings which share an adjacent pair of atoms) having 3 to 10 carbon atoms and in the ring(s) one or more atoms selected from the group consisting of N, O and S wherein one or more rings do not have a completely conjugated pi-electron system.

The term "$C_{1-20}$ alkoxy" refers to an —O—$C_{1-4}$alkyl group as defined herein.

The term "$C_{1-20}$ alkyl alcohol" refers to an —ROH group in which R is $C_{1-20}$ alkyl as defined herein.

The term "hydroxy" refers to an —OH group.

The term "halo" refers to chlorine, bromine, iodine or fluorine.

The term "cyano" refers to a —CN group.

The term "thiohydroxy" refers to a —SH group.

The term "amino" refers to an —NH$_2$ group.

The term "carbonyl" refers to a —C(=O)-R group, where R is selected from the group consisting of a hydrogen, a $C_{1-6}$ alkyl, a $C_{2-6}$ alkenyl, a $C_{2-6}$ alkynyl, a $C_{3-6}$ cycloalkyl, a $C_{4-6}$ aryl, and a $C_{3-6}$ heteroaryl (bonded through a ring carbon).

The term "sulfonyl" refers to a —S(=O)$_2$R" group with R being a $C_{1-6}$ alkyl.

The term "sulfamoyl" refers to a —S(=O)$_2$—NR$_x$R$_y$ group or a R$_y$S(O)$_2$—NR$_x$— group or, where R$_x$ and R$_y$ are selected from the group consisting of hydrogen, a $C_{1-6}$ alkyl, a $C_{2-6}$ alkenyl, a $C_{2-6}$ alkynyl, a $C_{3-6}$ cycloalkyl, a $C_{4-6}$ aryl, and a $C_{3-6}$ heteroaryl (bonded through a ring carbon).

The term "carbamoyl" refers to a —OC(=O)NR$_x$R$_y$ group or a R$_x$OC(=O)NR$_y$— group, with R$^x$ and R$^y$ independently being H or a $C_{1-6}$ alkyl.

The term "a $C_{1-20}$ haloalkyl" refers to a $C_{1-20}$ alkyl substituted by at least one halogen atom.

The term "a $C_{1-20}$ haloalkylthio" refers to a —SR group where R is a $C_{1-20}$ alkyl substituted by at least one halogen atom.

The term "$C_{1-20}$ alkylamino" refers to a —RNH$_2$ group where R is a $C_{1-20}$ alkyl.

The term "$C_{1-20}$ alkylsulfonyl" refers to a —S(=O)$_2$R group where R is a $C_{1-20}$ alkyl.

The term "$C_{1-20}$ haloalkylsulfonyl" refers to a —S(=O)$_2$R group where R is $C_{1-20}$alkyl substituted by at least one halogen atom.

The term "$C_{1-20}$ alkoxycarbonyl" refers to a —C(=O)OR group where R is a $C_{1-20}$ alkoxy.

The term "$C_{1-4}$ alkoxylcarbamoyl" refers to a —OC(=O)NR$_x$R$_y$ group or a R$_x$OC(=O)NR$_y$— group where R$_x$ is a $C_{1-4}$ alkyl.

The term "ureido" refers to a —NR$^x$C(=O)NR$^y$R$^z$ group, with R$^x$, R$^y$, and R$^z$ independently being H or a $C_{1-6}$ alkyl.

The term "amido" refers to a —C(=O)NR$^x$R$^y$ or a —R$^x$C(=O)NR$^y$— group, with R$^x$ and R$^y$ independently being H or a $C_{1-6}$ alkyl. The term "$C_{1-20}$ alkylamido" refers to amido as defined herein wherein R$_x$ is a $C_{1-20}$ alkyl.

In an embodiment, the compound represented by Formula 1 may be a disubstituted 1,2,3-triazoles. In a preferred embodiment, the compound represented by Formula 1 may be a 1-,4-disubstituted 1,2,3 -triazoles.

Hereinafter, the syntheses of substituted 1,2,3-triazoles of the present invention are presented, and the syntheses of substituted 1,2,3-triazoles of the present invention all start with N-Boc protected triazoles.

The following scheme 1 shows the synthesis of N-Boc protected triazoles:

Scheme 1

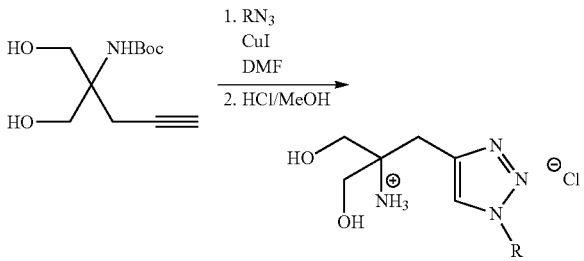

As shown in Scheme 1, alkynes (such as tent-butyl-1-hydroxy-2-(hydroxymethyl)pent-4-yn-2-ylcarbamates) and alkyl azides (such as $C_8H_{17}N_3$, $C_{12}H_{25}N_3$ etc.) were added to DMF in the presence of CuI, and stirred at room temperature to synthesize 4-substituted-N1-alkyl-1,2,3-triazoles under Cu(I)-catalyzed [3+2] cycloaddition reaction. The yield of the reaction was about 80% to 85%. Then the obtained N-Boc protected triazoles were stirred at room temperature under acidic condition (methanolic HCl) to get the desired triazolyl ammonium chloride compounds. The yield of the reaction was about 90% to 92%.

The syntheses of substituted 1,2,3-triazoles of the present invention starting with N-Boc protected triazoles follow Standard Procedure A:

10% methanolic HCl (0.84 mmol, 10.0 equiv, 0.3 mL) was added to a solution of Boc protected amine compound (0.084 mmol, 1.0 equiv) in methanol (1.0 mL). The resulted solution was stirred at room temperature for 6 h, and then excess solvent was evaporated under vacuum. The crude product was stirred in diethyl ether, and filtered to harvest the desired amine compounds 1-12.

The following examples are the synthesis of substituted 1,2,3-triazoles of the present invention.

EXAMPLE

Example 1

The synthesis of 2-Amino-2-((1-tetradecyl-1H-1,2,3-triazol-4-yl)methyl)propane-1,3-diol hydrochloride (compound 1)

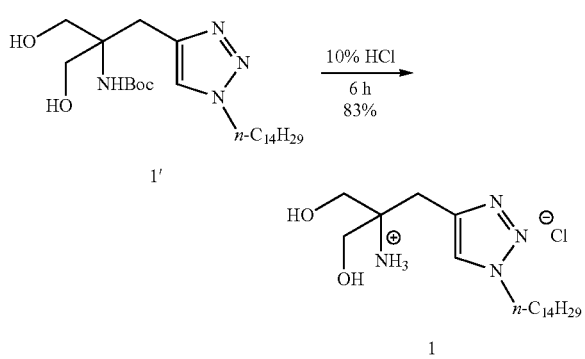

Boc compound 1' (40.2 mg, 0.086 mmol), 10% methanolic HCl (0.32 mL, 0.86 mmol), and methanol (1.0 mL) were used in Standard Procedure A. The crude product was stirred in diethyl ether, and filtered to harvest the compound 1 (28.5 mg, 0.071 mmol, 83%) as a white solid.

$^1$H NMR (300 MHz, (CD$_3$)$_2$SO) δ 7.97 (s, 1H), 7.90 (s, 3H), 4.32 (t, J=7.1 Hz, 2H), 3.43 (s, 4H), 2.93 (s, 2H), 1.80-1.78 (m, 2H), 1.22 (s, 22H), 0.84 (t, J=6.3 Hz, 3H); $^{13}$C NMR (75 MHz, (CD$_3$)$_2$SO) δ 140.2, 124.8, 60.9, 60.4, 49.7, 31.5, 30.3, 29.2, 28.9, 28.6, 28.4, 26.8, 26.1, 22.3, 14.1; HRMS (ESI$^-$) calcd for [M–H]$^-$ (C$_{20}$H$_{40}$ClN$_4$O$_2$) 403.2840, found 403.2840.

Example 2

The synthesis of 2-Amino-2-((1-hexadecyl-1H-1,2,3-triazol-4-yl)methyl)propane-1,3-diol hydrochloride (compound 2)

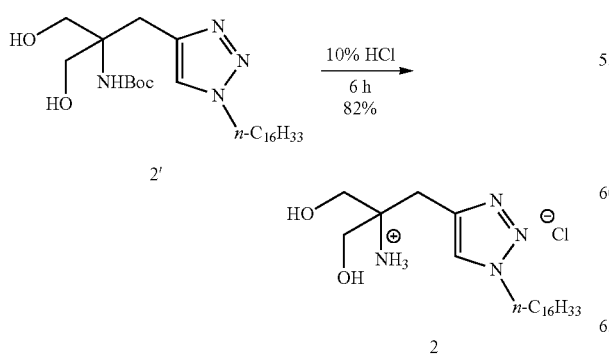

Boc compound 2' (40.8 mg, 0.082 mmol), 10% methanolic HCl (0.3 mL, 0.82 mmol), and methanol (1.0 mL) were used in Standard Procedure A. The crude product was stirred in diethyl ether, and filtered to harvest the compound 2 (29.1 mg, 0.067 mmol, 82%) as a white solid.

$^1$H NMR (300 MHz, (CD$_3$)$_2$SO) δ 7.96 (s, 1H), 7.87 (s, 3H), 4.33 (t, J=6.9 Hz, 2H), 3.43 (s, 4H), 2.93 (s, 2H), 1.81-1.75 (m, 2H), 1.23 (s, 26H), 0.85 (t, J=6.5 Hz, 3H); $^{13}$C NMR (75 MHz, (CD$_3$)$_2$SO) δ 140.4, 124.9, 61.1, 60.6, 49.8, 31.7, 30.1, 29.5, 29.49, 29.48, 29.47, 29.45, 29.3, 29.1, 28.8, 28.6, 27.5, 27.1, 26.3, 14.1; HRMS (ESI$^-$) calcd for [M–H]$^-$ (C$_{22}$H$_{44}$ClN$_4$O$_2$) 431.3153, found 431.3153.

Example 3

The synthesis of 2-Amino-2-((1-octadecyl-1H-1,2,3-triazol-4-yl)methyl)propane-1,3-diol hydrochloride (compound 3)

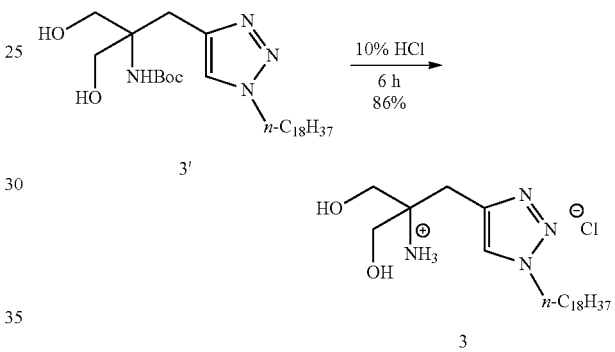

Boc compound 3' (40.9 mg, 0.078 mmol), 10% methanolic HCl (0.28 mL, 0.78 mmol), and methanol (1.0 mL) were used in Standard Procedure A. The crude product was stirred in diethyl ether, and filtered to harvest the compound 3 (30.8 mg, 0.067 mmol, 86%) as a white solid.

$^1$H NMR (300 MHz, (CD$_3$)$_2$SO) δ 7.99 (s, 1H), 7.94 (s, 3H), 4.29 (t, J=6.6 Hz, 2H), 3.43 (s, 4H), 2.94 (s, 2H), 1.81-1.73 (m, 2H), 1.21 (s, 30H), 0.83 (t, J=6.2 Hz, 3H); $^{13}$C NMR (75 MHz, (CD$_3$)$_2$SO) δ 140.5, 124.8, 61.2, 60.6, 49.8, 31.7, 30.1, 29.49, 29.48, 29.47, 29.46, 29.3, 29.1, 28.9, 27.2, 26.3, 14.1; HRMS (ESI$^-$) calcd for [M–H]$^-$ (C$_{24}$H$_{48}$ClN$_4$O$_2$) 459.3466, found 459.3468.

The synthesis of 2-Amino-2-(2-(1-octadecyl-1H-1,2,3-triazol-4-yl)ethyl)propane-1,3-diol hydrochloride (compound 4)

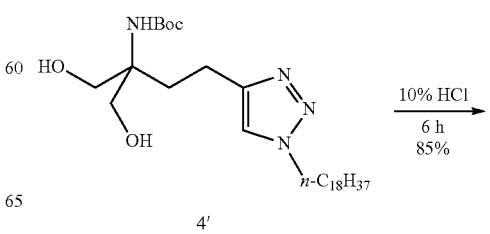

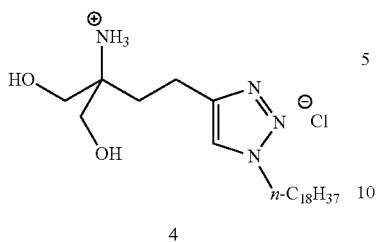

4

Boc compound 4' (49.5 mg, 0.093 mmol), 10% methanolic HCl (0.33 mL, 0.93 mmol), and methanol (1.2 mL) were used in Standard Procedure A. The crude product was stirred in diethyl ether, and filtered to harvest the compound 4 (37.5 mg, 0.079 mmol, 85%) as a white solid.

$^1$H NMR (300 MHz, (CD$_3$)$_2$SO) δ7.84 (s, 4H), 4.28 (t, J=7.1 Hz, 2H), 2.51 (t, J=6.9 Hz, 2H), 1.90-1.74 (m, 4H), 1.23 (s, 30H), 0.85 (t, J=6.2 Hz, 3H); $^{13}$C NMR (75 MHz, (CD$_3$)$_2$SO) δ 146.6, 122.2, 61.4, 60.5, 49.7, 31.7, 31.1, 30.2, 29.4, 29.3, 29.1, 28.9, 26.3, 22.5, 19.2, 14.4; HRMS (ESI) calcd for [M−H]$^-$ (C$_{25}$H$_{50}$N$_4$O$_2$Cl) 473.3622, found 473.3616.

The synthesis of 2-Amino-2-((1-pentadecyl-1H-1,2,3-triazol-4-yl)methyl)propane-1,3-diol hydrochloride (compound 5)

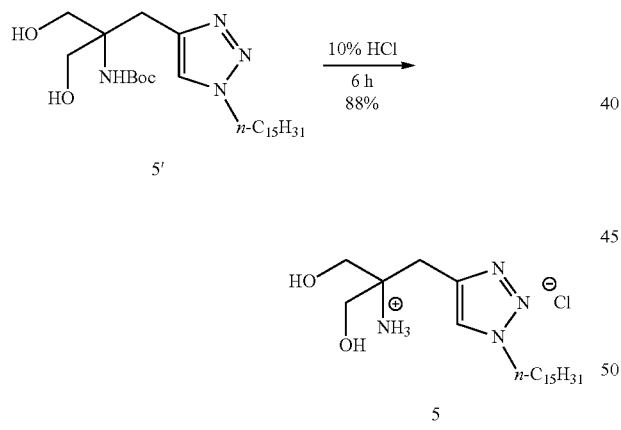

Boc compound 5' (40.5 mg, 0.084 mmol), 10% methanolic HCl (0.3 mL, 0.84 mmol), and methanol (1.0 mL) were used in Standard Procedure A. The crude product was stirred in diethyl ether, and filtered to harvest the compound 5 (30.9 mg, 0.073 mmol, 85%) as a white solid.

$^1$H NMR (300 MHz, (CD$_3$)$_2$SO) δ 7.97 (s, 4H), 4.28 (t, J=7.1 Hz, 2H), 3.41 (s, 4H), 2.94 (s, 2H), 1.76-1.75 (m, 2H), 1.19 (s, 24H), 0.81 (t, J=6.2 Hz, 3H); $^{13}$C NMR (75 MHz, (CD$_3$)$_2$SO) δ 140.5, 125.1, 61.1, 60.6, 49.9, 31.7, 30.1, 29.52, 29.51, 29.49, 29.48, 29.47, 29.44, 29.35, 29.18, 28.9, 27.1, 26.3, 22.6, 14.4; HRMS (ESI$^-$) calcd for [M−H]$^-$ (C$_{21}$H$_{42}$ClN$_4$O$_2$) 417.2996, found 417.2987.

The synthesis of 2-Amino-2-(2-(1-hexadecyl-1H-1,2,3-triazol-4-yl)ethyl)propane-1,3-diol hydrochloride (compound 6)

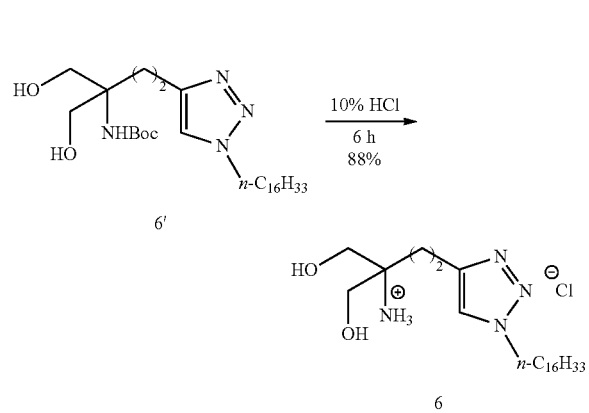

Boc compound 6' (21.2 mg, 0.042 mmol), 10% methanolic HCl (0.15 mL, 0.42 mmol), and methanol (0.5 mL) were used in Standard Procedure A. The crude product was stirred in diethyl ether, and filtered to harvest the compound 6 (16.3 mg, 0.036 mmol, 88%) as a white solid.

$^1$H NMR (300 MHz, (CD$_3$)$_2$SO) δ 7.83 (s, 1H), 7.79 (s, 3H), 4.28 (t, J=7.2 Hz, 2H), 3.51 (s, 4H), 2.51-2.49 (m, 2H), 1.90-1.76 (m, 4H), 1.23 (s, 26H), 0.85 (t, J=6.8 Hz, 3H); $^{13}$C NMR (75 MHz, (CD$_3$)$_2$SO) δ 146.6, 122.2, 61.3, 60.5, 49.7, 31.7, 31.1, 30.2, 29.5, 29.3, 29.1, 28.8, 26.3, 22.5, 19.2, 14.4; HRMS (ESI$^-$) calcd for [M−H]$^-$ (C$_{23}$H$_{46}$ClN$_4$O$_2$) 445.3309, found 445.3307.

The synthesis of Diethyl 2-amino-2-((1-octadecyl-1H-1,2,3-triazol-4-yl)methyl)malonate hydrochloride (compound 7)

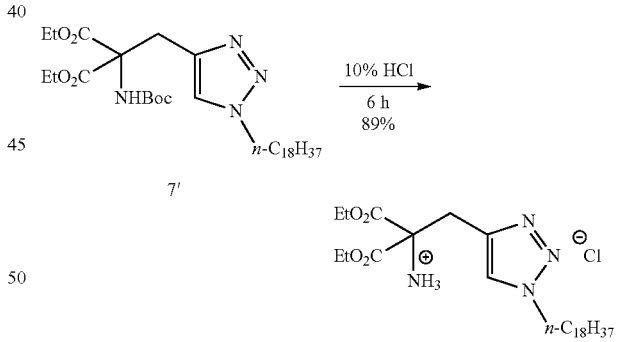

Boc compound 7' (40.2 mg, 0.066 mmol), 10% methanolic HCl (0.25 mL, 0.66 mmol), and methanol (0.8 mL) were used in Standard Procedure A. The crude product was stirred in diethyl ether, and filtered to harvest the compound 7 (32.2 mg, 0.059 mmol, 89%) as a white solid.

$^1$H NMR (300 MHz, (CD$_3$)$_2$SO) δ 9.25 (s, 3H), 7.98 (s, 1H), 4.31-4.22 (m, 6H), 3.53 (s, 2H), 1.77-1.75 (m, 2H), 1.23 (s, 36H), 0.85 (t, J=6.5 Hz, 3H); $^{13}$C NMR (75 MHz, (CD$_3$)$_2$SO) δ 165.3, 138.7, 125.3, 65.8, 63.7, 49.8, 31.7, 30.1, 29.4, 29.1, 28.9, 26.2, 22.5, 14.3, 14.1; HRMS (ESI) calcd for [M−H]$^-$ (C$_{28}$H$_{52}$ClN$_4$O$_4$) 543.3674, found 543.3677.

The synthesis of 2-Amino-2-((1-icosyl-1H-1,2,3-triazol-4-yl)methyl)propane-1,3-diol hydrochloride (compound 8)

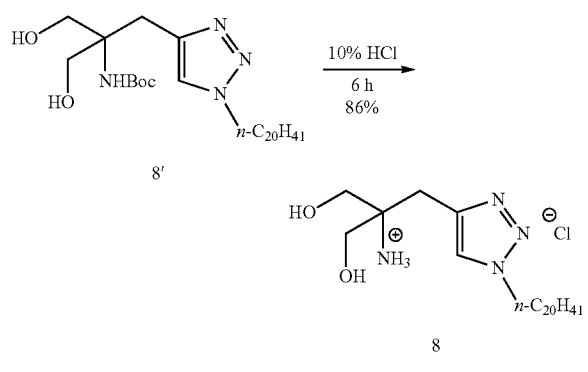

Boc compound 8' (30.6 mg, 0.055 mmol), 10% methanolic HCl (0.2 mL, 0.55 mmol), and methanol (0.6 mL) were used in Standard Procedure A. The crude product was stirred in diethyl ether, and filtered to harvest the compound 8 (23.1 mg, 0.047 mmol, 86%) as a white solid.

$^1$H NMR (300 MHz, (CD$_3$)$_2$SO) δ 8.02 (s, 1H), 7.97 (s, 3H), 4.29 (t, J=7.5 Hz, 2H), 3.43 (s, 4H), 2.95 (s, 2H), 1.81-1.74 (m, 2H), 1.21 (s, 34H), 0.83 (t, J=6.3 Hz, 3H); $^{13}$C NMR (75 MHz, (CD$_3$)$_2$SO) δ 140.5, 124.9, 61.1, 60.6, 49.8, 31.7, 30.1, 29.5, 29.4, 29.3, 29.2, 28.9, 27.1, 26.3, 22.6, 14.4; HRMS (ESI$^-$) calcd for [M–H]$^-$ (C$_{26}$H$_{52}$ClN$_4$O$_2$) 487.3779, found 487.3779.

The synthesis of 2-Amino-2-(3-(1-tetradecyl-1H-1,2,3-triazol-4-yl)propyl)propane-1,3-diol hydrochloride (compound 9)

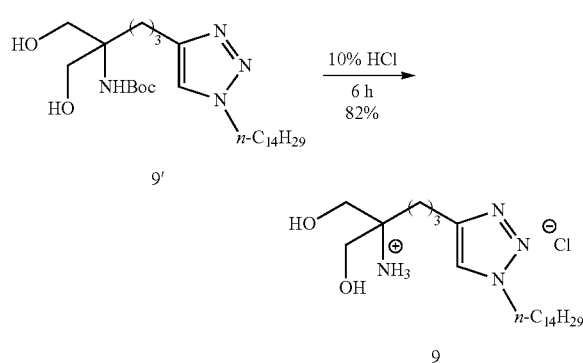

Boc compound 9' (30.3 mg, 0.061 mmol), 10% methanolic HCl (0.2 mL, 0.61 mmol), and methanol (0.6 mL) were used in Standard Procedure A. The crude product was stirred in diethyl ether, and filtered to harvest the compound 9 (21.5 mg, 0.05 mmol, 82%) as a white solid.

$^1$H NMR (300 MHz, (CD$_3$)$_2$SO) δ 7.91 (s, 1H), 7.79 (s, 3H), 4.28 (t, J=6.9 Hz, 2H), 3.44 (s, 4H), 2.58-2.51 (m, 2H), 1.79-1.75 (m, 2H), 1.59 (s, 4H), 1.22 (s, 22H), 0.84 (t, J=6.3 Hz, 3H); $^{13}$C NMR (75 MHz, (CD$_3$)$_2$SO) δ 146.6, 122.4, 61.3, 60.7, 49.7, 31.7, 30.9, 30.1, 29.5, 29.3, 29.1, 28.8, 26.3, 25.8, 22.6, 22.5, 14.4; HRMS (ESI$^-$) calcd for [M–H]$^-$ (C$_{22}$H$_{44}$ClN$_4$O$_2$) 431.3153, found 431.3149.

The synthesis of 2-Amino-2-(4-(1-tetradecyl-1H-1,2,3-triazol-4-yl)butyl)propane-1,3-diol hydrochloride (compound 10)

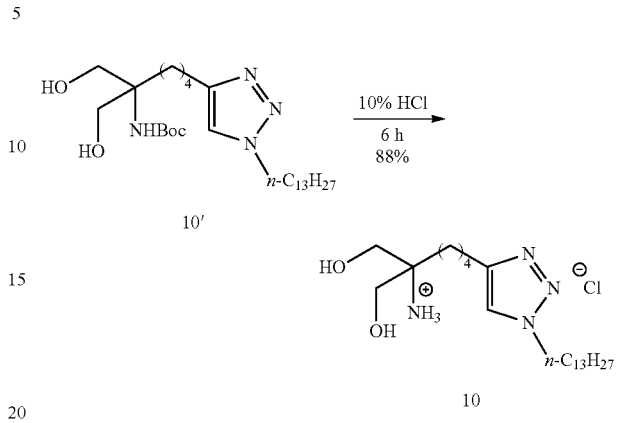

Boc compound 10' (20.3 mg, 0.041mmol), 10% methanolic HCl (0.15 mL, 0.41 mmol), and methanol (0.5 mL) were used in Standard Procedure A. The crude product was stirred in diethyl ether, and filtered to harvest the compound 10 (15.6 mg, 0.036 mmol, 88%) as a white solid.

$^1$H NMR (300 MHz, (CD$_3$)$_2$SO) δ 7.91 (s, 1H), 7.79 (s, 3H), 4.28 (t, J=6.9 Hz, 2H), 3.44 (s, 4H), 2.58-2.50 (m, 2H), 1.79-1.75 (m, 2H), 1.57-1.52 (m, 4H), 1.22 (s, 20H), 0.84 (t, J=6.3 Hz, 3H); $^{13}$C NMR (75 MHz, (CD$_3$)$_2$SO) δ 146.7, 122.6, 61.3, 60.5, 49.7, 31.7, 30.1, 29.4, 29.3, 29.1, 28.8, 26.3, 22.5, 19.2, 14.4; HRMS (ESI$^-$) calcd for [M–H]$^-$ (C$_{22}$H$_{44}$ClN$_4$O$_2$) 431.3153, found 431.3147.

The synthesis of 2-Amino-2-((1-tridecyl-1H-1,2,3-triazol-4-yl)methyl)propane-1,3-diol hydrochloride (compound 11)

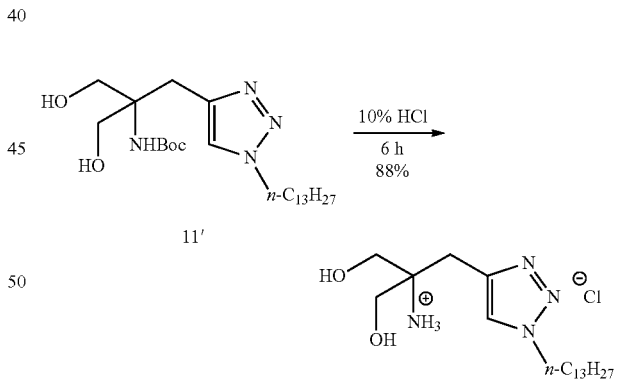

The Standard Procedure A was followed by use of boc compound 11' (30.5 mg, 0.067 mmol), 10% methanolic HCl (0.25 mL, 0.67 mmol), and methanol (0.8 mL). The crude product was stirred in diethyl ether, and filtered to harvest the compound 11 (23.2 mg, 0.059 mmol, 88%) as a white solid.

$^1$H NMR (300 MHz, (CD$_3$)$_2$SO) δ 8.04 (s, 1H), 7.97 (s, 3H), 4.29 (t, J=7.0 Hz, 2H), 3.43 (s, 4H), 2.95 (s, 2H), 1.77-1.70 (m, 2H), 1.21 (s, 20H), 0.83 (t, J=6.5 Hz, 3H); $^{13}$C NMR (75 MHz, (CD$_3$)$_2$SO) δ 143.1, 125.1, 61.1, 60.6, 49.9, 31.7, 30.1, 29.4, 29.3, 29.1, 28.9, 27.1, 26.3, 22.6, 14.4; HRMS (ESI−) calcd for [M−H]− ($C_{19}H_{38}ClN_4O_2$) 389.2683, found 389.2683.

The synthesis of 3-(1-Icosyl-1H-1,2,3-triazol-4-yl)-2-(methoxymethyl)-2-(methylamino)propan-1-ol (compound 12)

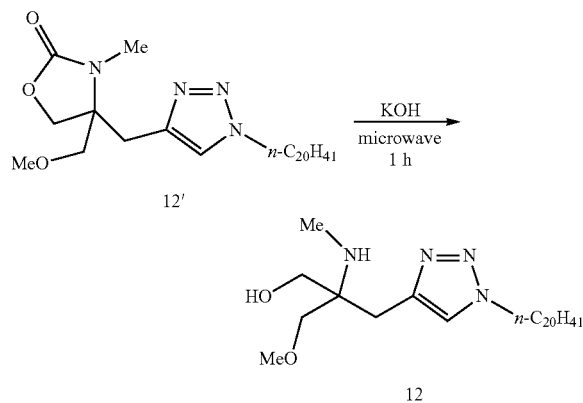

Potassium hydroxide (190.0 mg, 3.3862 mmol, 66.0 equiv) was added to a solution of compound 12' (26.1 mg, 0.051 mmol, 1.0 equiv), in ethanol (0.7 mL). The reaction was heated in microwave (150° C., 200 W) for 1 h, and then neutralized with 2N aqueous HCl solution. The reaction mass was extracted with dichloromethane (3×2 mL), dried over anhydrous magnesium sulphate, evaporated under vacuum. The crude product was purified by column chromatography ($SiO_2$: MeOH/$CHCl_3$, 1:1; $R_f$ 0.76) to harvest the compound 12 (16.3 mg, 0.033 mmol, 66%) as white solid.

$^1$H NMR (300 MHz, $CDCl_3$) δ 7.68 (s, 1H), 4.29 (t, J=7.2 Hz, 2H), 3.89 (d, J=12.9 Hz, 1H), 3.60-3.50 (m, 3H), 3.33 (s, 3H), 3.31-3.19 (m, 2H), 2.82 (s, 3H), 1.86-1.83 (m, 2H), 1.27 (s, 34H), 0.85 (t, J=6.6 Hz, 3H); $^{13}$C NMR (75 MHz, $CDCl_3$) δ 140.4, 124.1, 70.6, 64.8, 60.8, 59.3, 50.4, 31.8, 30.1, 29.6, 29.5, 29.4, 29.3, 28.9, 28.2, 26.5, 25.4, 22.6, 14.1; HRMS (ESI−) calcd for [M+H]+ ($C_{28}H_{57}N_4O_2$) 481.4482, found 481.4486.

The antineoplastic activities of 1,4-disubstituted 1,2,3-triazoles of the present invention are illustrated by the following examples.

Methods

Cell Lines and Cell Culture

Human hormone-refractory prostate cancer cell lines PC-3 and DU-145 were from American Type Culture Collection (Rockville, MD). Cells were cultured in RPMI 1640 medium with 10% FBS (v/v) and penicillin (100 U/ml)/streptomycin (100 μg/ml). Cultures were maintained in a humidified incubator at 37° C. in 5% $CO_2$/95% air.

Sulforhodamine B (SRB) Assays

Cells were seeded in 96-well plates in medium with 5% FBS. After 24 hours, cells were fixed with 10% TCA to represent cell population at the time of drug addition ($T_0$). After additional incubation of DMSO or the compound for 48 hours (PC-3 cells) or 72 hours (DU145 cells), cells were fixed with 10% TCA and SRB at 0.4% (w/v) in 1% acetic acid was added to stain cells. Unbound SRB was washed out by 1% acetic acid and SRB bound cells were solubilized with 10 mM Trizma base. The absorbance was read at a wavelength of 515 nm. Using the following absorbance measurements, such as time zero ($T_0$), control growth (C), and cell growth in the presence of the compound (Tx), the percentage growth was calculated at each of the compound concentrations levels. Percentage growth inhibition was calculated as: [1−(Tx−$T_0$)/(C−$T_0$)]×100%. Growth inhibition of 50% ($IC_{50}$) is determined at the compound concentration which results in 50% reduction of total protein increase in control cells during the compound incubation. Data are expressed as mean±SEM of three to five determinations.

The results of the above-mentioned assay were summarized in Table 1.

TABLE 1

| No. | Compound | M.w. | PC-3 cells $IC_{50}$ (μM) | DU-145 cells $IC_{50}$ (μM) |
|---|---|---|---|---|
| 1 | 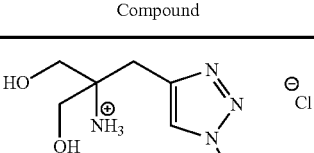 | 405.02 | 4.9 | 4.7 |
| 2 | 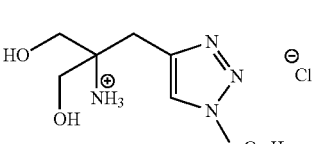 | 433.07 | 3.3 | 5.3 |
| 3 | 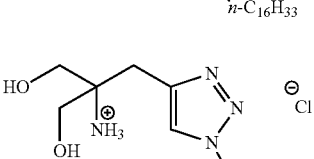 | 461.12 | 4.5 | 5.7 |

TABLE 1-continued

| No. | Compound | M.w. | PC-3 cells IC$_{50}$ (μM) | DU-145 cells IC$_{50}$ (μM) |
|---|---|---|---|---|
| 4 | (structure with n-C$_{18}$H$_{37}$) | 475.15 | 3.6 | 2.4 |
| 5 | (structure with n-C$_{15}$H$_{31}$) | 419.04 | 3.5 | — |
| 6 | (structure with n-C$_{16}$H$_{33}$) | 447.09 | 6.2 | — |
| 7 | (structure with EtO$_2$C groups, n-C$_{18}$H$_{37}$) | 545.19 | 7.9 | >10 |
| 8 | (structure with n-C$_{20}$H$_{41}$) | 489.18 | 3.8 | 6.2 |
| 9 | (structure with n-C$_{14}$H$_{29}$) | 433.07 | 4.2 | 5.4 |
| 10 | (structure with n-C$_{13}$H$_{27}$) | 433.07 | 8.97 | 6.20 |
| 11 | (structure with n-C$_{13}$H$_{27}$) | 390.99 | 5.31 | 4.20 |
| 12 | (structure with Me-NH, OMe, n-C$_{20}$H$_{41}$) | 480.77 | 2.99 | 4.68 |

IC$_{50}$ (half maximal inhibitory concentration) is used herein to indicate a measure of the effectiveness of the compound represented by Formula I in inhibiting PC-3 cells and DU-145 cells. IC$_{50}$ represents the concentration of the compound represented by Formula I that is required for 50% inhibition in vitro, and IC$_{50}$<10 μM indicates the compound is useful for inhibiting PC-3 cells and DU-145 cells. The lower the IC$_{50}$ Value, the more potent the drug is in vitro. As is apparent from Table 1, compounds 1-5, 8-9 and 12 exhibit excellent antineoplastic activity with an IC$_{50}$<5 μM in PC-3 cells, and compounds 6, 7, 10 and 11 exhibit antineoplastic activity with an IC$_{50}$<10 μM in PC-3 cells. Compounds 1, 4, 11 and 12 exhibit excellent antineoplastic activity with an $IC_{50}$<5 μM in DU-145 cells, and compounds 2, 3 and 8-10 exhibit antineoplastic activity with an $IC_{50}$<10 μM in DU-145 cells. Thus, substituted 1,2,3-triazoles of the present invention could be used as an active ingredient of the pharmaceutical composition for treating a mammal suffering from cancer or disease characterized by undesirable cell proliferation.

Accordingly, the compound represented by Formula I can be used as an antitumor agent.

Another object of the present invention is to provide a pharmaceutical composition comprising an effective amount of any one compound of the present invention and a carrier. The carrier in the pharmaceutical composition must be "acceptable" in the sense that it is compatible with the active ingredient of the composition (and preferably, capable of stabilizing the active ingredient) and not deleterious to the subject to be treated. Examples of other carriers include colloidal silicon oxide, magnesium stearate, cellulose, sodium lauryl sulfate, and D&C Yellow #10.

The pharmaceutical composition may further comprise an additive, wherein the additive may be a filler, a wetting agent, a binder, or a disintegrant, but the additive is not limited thereto. For example, other commonly used surfactants such as Tweens or Spans or other similar emulsifying agents or bioavailability enhancers which are commonly used in the manufacture of pharmaceutically acceptable solid, liquid, or other dosage forms can also be used as an additive for the purpose of formulation. And if desired, certain sweetening, flavoring, or coloring agents can be added.

The filler is one or more than one substance selected from the group consisting of lactose, sugar, starches, modified starches, mannitol, sorbitol, inorganic salts, cellulose derivatives (e.g. microcrystalline cellulose, cellulose), calcium sulfate, xylitol, lactitol, and the mixture thereof, but is not limited thereto.

The wetting agent is one or more than one substances selected from the group consisting of distilled water, ethanol, starch paste, and the mixture thereof, but is not limited thereto.

The binder is one or more than one selected from the group consisting of acacia, gelatin, tragacanth, dextrin, polyvinylpyrrolidone, starch and the derivative thereof, sodium alginate, sorbitol, syrup, hypromellose, methyl cellulose, hydroxypropyl cellulose, hydroxyethylcellulose, ethylcellulose, sodium carboxymethylcellulose, calcium carboxymethylcellulose, glucose, polymethacrylate, and the mixture thereof, but is not limited thereto.

The disintegrate is one or more than one substances selected from the group consisting of crosscarmellose sodium, crospovidone, polyvinylpyrrolidone, sodium starch glycollate, corn starch, microcrystalline cellulose, hydroxypropyl methylcellulose, hydroxypropyl cellulose, and the mixture thereof, but is not limited thereto.

Such a pharmaceutical composition can be in the form of tablets, capsules, powders, granules, suppositories, reconstitutable powders, liquid preparations for oral administration, nasal aerosols or inhalation compositions, or sterile injectable compositions, but is not limited thereto.

In the case of tablets, commonly used carriers include lactose and corn starch. In the case of capsules, useful carriers include lactose and dried corn starch. When liquid preparations are administered orally, the active ingredient can be suspended or dissolved in an oily phase combined with emulsifying or suspending agents.

In other embodiment, the pharmaceutical composition may be suppositories which may be dissolved completely in the rectum or vagina, respectively, or remain intact following release of the composition, and subsequently removed. In general, the suppositories of the pharmaceutical composition may be prepared by mixing the ingredients using techniques well known to those skilled in the art.

In an embodiment, the pharmaceutical composition may be nasal aerosols or inhalation compositions. The nasal aerosols or inhalation compositions may be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

In other embodiment, the pharmaceutical composition may be sterile injectable compositions. A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acid, such as oleic acid and its glyceride derivatives are useful in the preparation of injectable composition, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents.

Also within the scope of this invention is a method treating a cancer disease in an individual by administering an effective amount of the abovementioned pharmaceutical composition to a subject in need.

In an embodiment, the cancer disease is a prostate cancer and the prostate cancer has metastasized to a tissue selected from the group consisting of bone, lymph node, eye, pancreas, lung, adrenal gland, breast, kidney, muscle, salivary gland, spleen, brain and/or liver.

Administration of the compounds of this invention may be by any method used for administering therapeutics, such as for example oral, intravenous, intramuscular, subcutaneous, or rectal administration.

The dose of the compound used in the method will vary in the usual way with the weight and metabolic health of the patient, the severity of any side effects, and the relative efficacy of the compound employed when used against the type of tumor involved. The preferred initial dose for the general patient population will be determined by routine dose-ranging studies, as is conducted for example during clinical studies. Therapeutically effective doses for individual patients may be determined by titrating the amount of drug given to the individual to arrive at the desired therapeutic effect without incurring an unacceptable level of side effects, as is currently and routinely done with other forms of chemotherapy.

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiment(s) of the present invention.

What is claimed is:
1. A compound represented by one of compounds shown below:
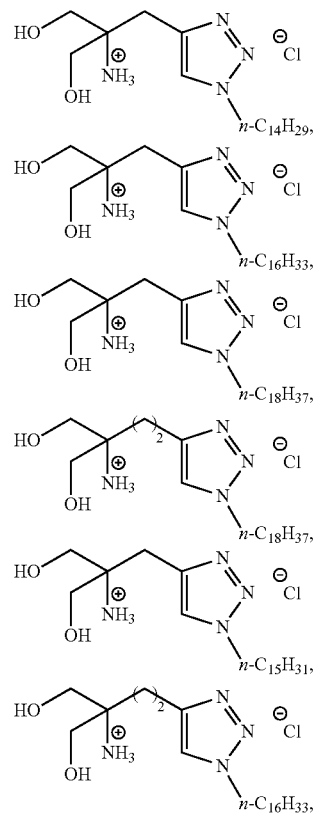
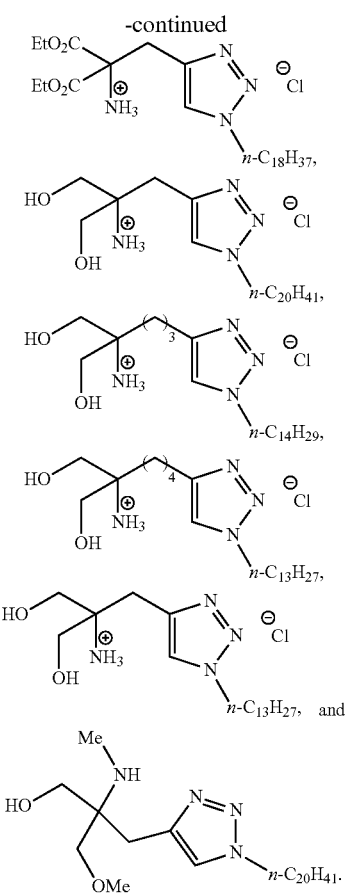
* * * * *